United States Patent [19]

Chen et al.

[11] Patent Number: 4,992,349
[45] Date of Patent: Feb. 12, 1991

[54] CYCLIC BIS-DICARBOXIMIDE CHARGE TRANSPORT COMPOUNDS FOR ELECTROPHOTOGRAPHY

[75] Inventors: Chin H. Chen, Fairport; Yann Hung, Rochester, both of N.Y.

[73] Assignee: Eastman Kodak Company, Rochester, N.Y.

[21] Appl. No.: 432,018

[22] Filed: Nov. 6, 1989

[51] Int. Cl.$^5$ .............................................. G03G 5/14
[52] U.S. Cl. ...................................... 430/58; 252/500
[58] Field of Search ........................................ 430/58

[56] References Cited

U.S. PATENT DOCUMENTS 4,175,960 11/1979 Berwick .............................. 430/58
4,442,193 4/1984 Chen .................................. 430/83

Primary Examiner—David Welsh
Attorney, Agent, or Firm—Dressler, Goldsmith, Shore, Sutker & Milnamow, Ltd.

[57] ABSTRACT

Cyclic bis-dicarboximides are employed as electron transport agents in photoconductor elements. Such compounds are characterized by the formula:

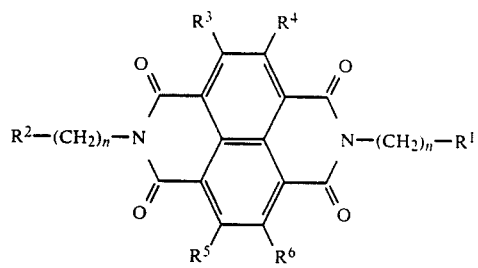

wherein:
$R^1$ and $R^2$, which may be the same or different, represent aryl, or aryl substituted with alkyl, alkoxy, perfluoroalkyl or perfluoroalkoxy groups having 2 to 20 carbon atoms; sulfonyl; sulfone; sulfonamide; nitrile; or nitro groups;
$R^3$, $R^4$, $R^5$, and $R^6$, which may be the same or different, represent hydrogen, alkyl having 1 to 4 carbon atoms, alkoxy having 1 to 4 carbon atoms, or halogen; and
n is 0 to 3.

10 Claims, No Drawings

CYCLIC BIS-DICARBOXIMIDE CHARGE TRANSPORT COMPOUNDS FOR ELECTROPHOTOGRAPHY

FIELD OF THE INVENTION

This invention is in the field of cyclic bis-dicarboximide compounds useful as charge transport agents in photoconductor elements.

BACKGROUND OF THE INVENTION

In multiactive photoconductor elements of the type employing a charge generating layer and a charge transport layer, it has been common to employ in the charge transport layer either a polymer, such as polyvinyl carbazole, or a composition comprised of an electron-donating, low molecular weight organic compound dissolved in an insulating binder polymer. Such charge transport layers commonly suffer from problems upon repeated use, such as high dark decay, fluctuations in surface potential, insufficient electron charge transport activity, a gradually increasing residual potential or the like. Consequently, the art of photoconductor elements continues to seek new charge transport agents which exhibit sufficient sensitivity, but which do not exhibit disadvantages such as above indicated which might restrict their utilization in positively charged photoconductor elements.

Certain charge transport agents, such as trinitrofluorenone (TNF), which do exhibit a useful level of sensitivity, suffer from the further disadvantage that they are now suspected to be carcinogens.

Although cyclic bis-dicarboximide compounds have previously been proposed for use as sensitizers for photoconductor materials (see U.S. Pat. No. 4,442,193), so far as now known, no one has heretofore proposed the use of cyclic bis-dicarboximides as charge transport agents in photoconductor elements.

SUMMARY OF THE INVENTION

This invention relates to the use of cyclic bis-dicarboximides as electron-transport agents in charge transport layers of photoconductor elements.

The cyclic bis-dicarboximides of the present invention are characterized by the formula:

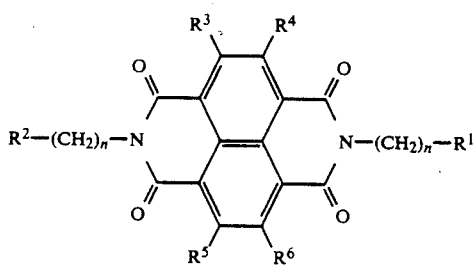

(1)

wherein:

$R^1$ and $R^2$, which may be the same or different, represent aryl, or aryl substituted with alkyl, alkoxy, perfluoroalkyl or perfluoroalkoxy groups having 2 to 20 carbon atoms; sulfonyl; sulfone; sulfonamide; nitrile; or nitro groups;

$R^3$, $R^4$, $R^5$, and $R^6$, which may be the same or different, represent hydrogen, alkyl having 1 to 4 carbon atoms, alkoxy having 1 to 4 carbon atoms, or halogen; and n is 0 to 3.

In one class of presently preferred compounds of Formula (1), $R^1$ and $R^2$ are each trifluoromethyl or pentafluoroethyl substituted phenyl or naphthyl groups.

In another class of presently preferred compounds of Formula (1), n is 0 and $R_1$ and $R_2$ are each phenyl substituted with either (a) electron donating groups, such as alkyl groups containing 2 through 6 carbon atoms each, or alkoxy groups containing 2 through 20 carbon atoms each, or (b) electron-withdrawing groups, such as sulfone, nitro, or trifluoromethyl (which last group is presently more preferred). Such substitutents may be on the ortho, meta, or para positions of the phenyl ring.

The compounds of Formula (1) when used as electron-transport agents in charge transport layers, particularly in positively charged photoconductor elements, display excellent electron charge transport capability.

The compounds of Formula (1) are not carcinogenic, are stable under ambient conditions are readily prepared, and can be readily compounded for utilization in a charge transport layer since such compounds are readily soluble in common organic solvents, especially chlorinated solvents.

For use in a charge transport layer, a compound of Formula (1) is dissolved or dispersed together with a preferably dissolved, insulating, film forming binder polymer in a solvent medium, such as a chlorinated hydrocarbon, or the like. This resulting composition is coated on a surface and then dried to provide the desired charge transport layer.

Cyclic dicarboximides of Formula 1 which are useful in the charge transport layers of this invention are preferably soluble to an extent of at least about 0.25 weight percent, and preferably to an extent of at least about 1 weight percent, in an organic solvent which is suitable for use as a coating solvent. Presently preferred solvents are halogenated hydrocarbons, such as 1,2-dichloroethane, 1,1,2-trichloroethane, 1,1,2- trichloropropane, 1,1,2,2-tetrachloroethane, dichloromethane, trichloromethane, and the like.

The compounds of Formula (1) are capable of being used in photoconductor elements in combination with electrically conductive layers and charge generation layers which are known to the art.

The compounds of Formula (1) are substantially completely transparent to visible and near infrared region light so that little or no loss in incident light occurs as such light passes through a charge transport layer of this invention.

The compounds of Formula (1), if desired, may be used in combination with prior art hole or p-type charge transport agents in an insulating binder polymer to form charge transport layers exhibiting bipolar charge-transport characteristics.

The compounds of Formula (1), if desired, may be used in combination with prior art electron or n-type charge transport agents in an insulating binder polymer in charge transport layers.

The present invention thus relates to new multiactive photoconductor elements which employ at least one compound of Formula (1) in a charge transport layer.

Other and further aims, purposes, features, advantages, and the like will be apparent to those skilled in the art from the teachings of the present specification taken with the appended claims.

DETAILED DESCRIPTION OF THE INVENTION

The term "lower" as used herein in reference to a group, such as alkyl, or the like, means that such group contains less than 7 carbon atoms. Such a group, when it contains three or more carbon atoms, can be straight or branched chain.

The term "aryl" or "aryl group" as used herein means both unsubstituted aryl groups, such as phenyl or naphthyl, and substituted aryl groups.

The term "substituted" as used herein in reference to a group, such as aryl group, or the like, means that such group is substituted by a group, such as lower alkyl; lower alkylene; nitro; halo; primary, secondary, or tertiary amino; cyano; sulfate; and the like.

The term "halogen" as used herein means fluorine, chlorine, bromine or iodine.

The synthesis of symmetrical compounds of Formula (1) is accomplished by azeotropic refluxing of two equivalents of primary amine with one equivalent of 1,4,5,8-naphthalenetetracarboxylic dianhydride. The refluxing is accomplished in a high boiling solvent, such as diphenyl ether-biphenyl-eutectic (available commercially from Dow Chemical Company as Dowtherm ™ A, boiling point (bp) 253° C.).

The reaction is illustrated below. Compounds usually precipitate on cooling, and, if desired, can be further purified by recrystalization from p-dioxane.

The synthesis of unsymmetrical compounds of Formula (1) is accomplished by selectively reacting, in the same manner, one equivalent of an appropriate amine with a slight molar excess of a dianhydride to give the monoanhydride which can then be reacted further, with a different primary amine to give a desired unsymmetrical compound, as illustrated below.

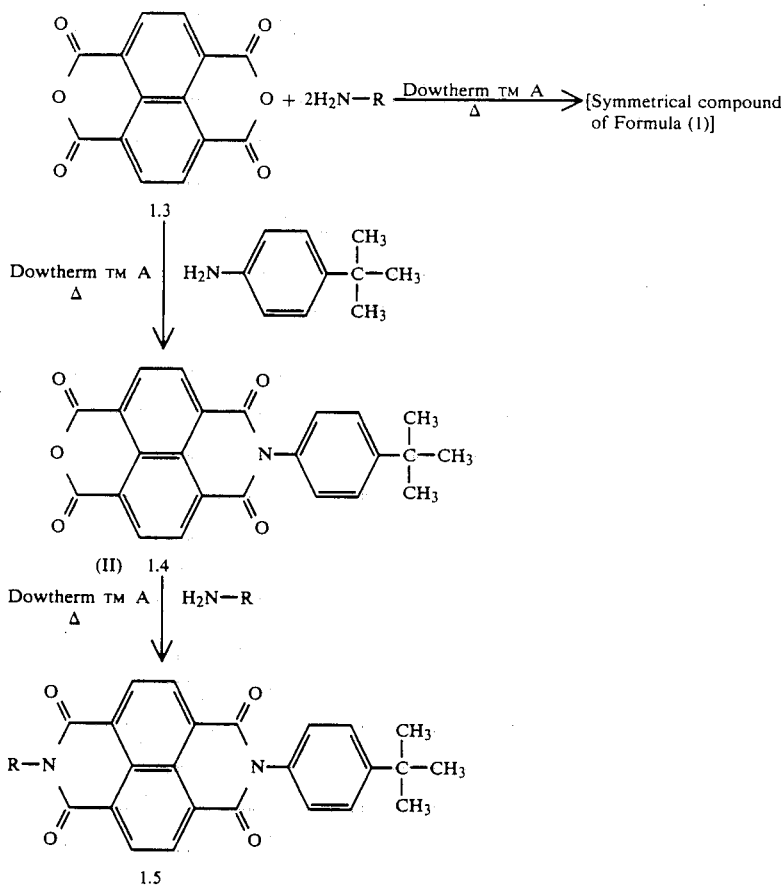

It is presently preferred to employ p-(t-butyl)aniline for the unsymmetrical synthesis because its bis-derivative displays solubility in methylene chloride.

It is presently preferred to use a slight excess of the dianhydride because the dianhydride is the least soluble of the reactants in the reaction mixture and can be readily removed from the monoanhydride by filtration. Also, in this manner, the formation of the undesirable bis-derivative can be kept to a minimum.

All of the compounds can be decolorized with charcoal and recrystallized from p-dioxane.

Compounds of Formula (1) display useful electron transport capability when dissolved in an insulating organic binder polymer and formed into a charge transport layer of a photoconductor element. These compounds are particularly useful as electron-transport agents in positively-charged photoconductor elements.

Because of their electron transport capability and solubility characteristics in dichloromethane and trichloromethane, bis-p-(D-butyl) phenylated derivatives of Formula (1) are presently particularly preferred for use in the practice of this invention. For example, these derivatives have a solubility of about 2% (g/ml) in $CH_2Cl_2$ and a solubility of about 4% (g/ml) in $CHCl_3$. In addition, they have good electron transport capability in photoconductor elements.

A presently preferred class of photoconductor elements of this invention comprises:
(a) a substrate;
(b) an electrically conductive layer;
(c) a charge generation layer; and
(d) a charge transport layer comprising a polymeric binder in which is dissolved at least one cyclic bis-dicarboximide of Formula (1).

Photoconductor elements of this invention having a compound of Formula (1) in the charge transport layer display photosensitivity in the spectral range of about 400 to about 900 nm. The exact photosensitivity achieved in any given photoconductor element is dependent upon the photoresponse of the charge generation layer. The term "photosensitivity" or "photo response" as used herein means the capacity, of a compound to be stimulated by light. For purposes of the present invention, photosensitivity is conveniently measured by corona charging the element to a certain potential, exposing the charged element to a monochromatic light and measuring the decrease of the surface potential. The amount of light necessary to discharge the element to a certain potential is defined as "photosensitivity."

The photoconductor elements of this invention can employ conventional substrates, such as a film or sheet material, as the support layer. The support layer is relatively thermally stable, electrically insulating, and has dielectric strength. Examples of polymers used in films include cellulose acetate, polystyrene, polycarbonates, polyesters, such as polyethylene terephthalate, and the like. Presently preferred substrates are polyethylene terephthalate and polycarbonates. Typical film support layers have a thickness in the range of about 100 microns, although thicker and thinner layers can be employed.

The photoconductor elements of this invention can employ various electrically conductive layers. For example, the conductive layer can be a metal foil which is conventionally laminated to the support layer. Suitable metal foils include those comprised of aluminum, zinc, copper, and the like. The support layer and the conductive layer can be formulated as a consolidated layer which can be a metal plate. For example, suitable plates can be formed of metals, such as aluminum, copper, zinc, brass and galvanized steel. Alternatively, vacuum deposited metal layers upon a substrate are suitable and are presently preferred, such as vapor deposited silver, nickel, gold, aluminum, chromium, and metal alloys. The thickness of a vapor deposited metal layer can be in the range of about 20 to about 500 angstroms. Conductive layers can also comprise a particulate or dissolved organic or inorganic conductor or semi-conductor distributed in a binder resin. For example, a conductive layer can comprise compositions of protective inorganic oxide and about 30 to about 70 weight percent of conductive metal particles, such as a vapor deposited conductive cermet layer as described in U.S. Pat. No. 3,880,657. Also see in this connection the teachings of U.S. Pat. No. 3,245,833 relating to conductive layers employed with barrier layers. Organic conductive layers can be employed, such as those comprised of a sodium salt of a carboxyester lactone of maleic anhydride in a vinyl acetate polymer, as taught, for example in U.S. Pat. Nos. 3,007,901 and 3,262,807.

In the photoconductor elements of the invention, the conductive layer is optionally but preferably overcoated by a barrier adhesive or subbing layer. The barrier layer typically has a dry thickness in the range of about 0.01 to about 5 microns. Typical subbing layers are solvent soluble, film-forming polymers, such as, for example, cellulose nitrate, polyesters, copolymers of poly(vinyl pyrrolidone) and vinylacetate, and various vinylidene chloride-containing polymers, including 2, 3 and 4 component polymers prepared from a polymerizable blend of monomers or prepolymers containing at least 60% by weight of vinylidene chloride. Representative vinylidene chloride-containing polymers include vinylidene chloride-methyl methacrylate-itaconic acid terpolymers such as disclosed in U.S. Pat. No. 3,143,421. Various vinylidene chloride-containing hydrogel tetrapolymers which may be used include tetrapolymers of vinylidene chloride, methyl acrylate, acrylonitrile and acrylic acid, such as disclosed in U.S. Pat. No. 3,640,780. Other useful vinylidene chloride-containing copolymers include poly(vinylidene chloride-methyl acrylate), poly(vinylidene chloride-methacrylonitrile) poly(vinylidene chloride-acrylonitrile), and poly(vinylidene chloride-acrylonitrile-methyl acrylate). Other subbing materials include the so called tergels described in U.S. Pat. No. 3,501,301 and the vinylidene chloride terpolymers described in U.S. Pat. No. 3,228,770. One useful class of subbing layers is comprised of a hydrophobic film-forming polymer or copolymer that is free from any acid-containing group, such as a carboxyl group, that is prepared from a blend of monomers or prepolymers, each of said monomers or prepolymers containing one or more polymerizable ethylenically unsaturated groups. Examples of such a polymer include many of the aforenamed copolymers, and, in addition, copolymers of polyvinylpyrrolidone and vinyl acetate, poly(vinylidene chloride-methyl methacrylate), and the like. Presently preferred subbing layers are comprised of polyesters and poly(vinylidene-acrylonitrile).

While any convenient method of application of a subbing layer can be used, it is presently preferred to dissolve the polymer in a solvent, and then to coat the solution over the conductive layer.

The barrier layer coating composition can also contain minor amounts of various optional additives, such as surfactants, levelers, plasticizers, and the like.

Mixtures of different solvents or liquids can be employed Preferably, the solvents are volatile, that is, evaporable, at temperatures below about 150° C. Examples of suitable solvents include aromatic hydrocarbons, such as benzene, toluene, xylene, mesitylene, etc.; ketones, such as acetone, 2-butanone, etc.; ethers, such as tetrahydrofuran, methyl ethyl ether, petroleum ether, etc.; alkanols, such as isopropyl alcohol, etc.; halogenated aliphatic hydrocarbons, such as methylene dichloride, chloroform, and ethylene chloride, etc.; and the like. Presently preferred coating solvents are chlorinated aliphatic hydrocarbons, and the like.

The barrier layer coating composition is applied by using a technique such as knife coating spray coating, swirl coating, extrusion hopper coating or the like. After application, the coating composition is conveniently air dried.

The charge generation layer is applied over the conductive layer, or over the barrier layer, if a barrier layer is employed.

The charge generating (or generation) layer is conveniently comprised of at least one conventional photoconductor (or photoconductive agent) that is typically dispersed in a polymeric binder. The layer can have a thickness that varies over a wide range, typical layer thicknesses being in the range of about 0.05 to about 5 microns As those skilled in the art will appreciate, as layer thickness increases, a greater proportion of incident radiation is absorbed by a layer, but the likelihood increases of trapping a charge carrier which then does not contribute to image formation. Thus, an optimum thickness of a layer can constitute a balance between these competing influences.

Photoconductors suitable for use in the charge generating layer include organic compounds which exhibit photoconductivity. The term "photoconductivity" as used herein means the increase in electrical conductivity displayed by a non-metallic solid when it absorbs electromagnetic radiation. For purposes of this invention, a photoconductor in the dark is electrically insulating, but, upon exposure to actinic radiation, becomes electrically conductive The dark resistivity of a photoconductor used in the practice of this invention is preferably greater than about $10''$ ohm-isopropyl centimeters (ohm-cm) at 25° C. and is rapidly reduced by several orders of magnitude when exposed to actinic radiation at an intensity of about 1 to about 30 ergs per sq. cm per sec. (ergs/cm$^2$/sec).

A wide variety of photoconductors can be employed, including inorganic, and organic/photoconductors. Inorganic materials include, for example, zinc oxide, lead oxide, and selenium. Organic materials include various particulate organic pigment materials, such as phthalocyanine pigments, and a wide variety of soluble organic compounds including metallo-organic and polymeric organic photoconductors. A partial listing of representative photoconductive materials may be found, for example, in Research Disclosure, Vol. 109, May, 1973, page 61, in an article entitled "Electrophotographic Elements, Materials and Processes", at paragraph IV(A) thereof. This partial listing of well-known photoconductive materials is hereby incorporated by reference.

Examples of suitable organic photoconductors include phthalocyanine pigments, such as a bromoindium phthalocyanine pigment described in U.S. Pat. No. 4,727,139 or a titanylphthalocyanine pigment described in U.S. Pat. No 4,701,396; various pyrylium dye salts, such as pyrylium, bispyrylium, thiapyrylium, and selenapyrylium dye salts, as disclosed, for example, in U.S. Pat. No. 3,250,615; fluorenes, such as 7,12-dioxo-13-dibenzo(a,h)fluorene, and the like; aromatic nitro compounds of the kind disclosed in U.S. Pat. No. 2,610,120; anthrones such as those disclosed in U.S. Pat. No. 2,670,284; quinones such as those disclosed in U.S. Pat. No. 2,670,286; benzophenones, such as those disclosed in U.S. Pat. No 2,670,287; thiazoles, such as those disclosed in U.S. Pat. No. 3,732,301; various dyes such as cyanine (including carbocyanine, merocyanine, diarylmethane, thiazine, azine, oxazine, xanthene, phthalein, acridine, azo, anthraquinone dyes, and the like, and mixtures thereof.

The photoconductor, or a mixture of photoconductors, is usually applied from a solution in a coating composition to form a charge generating layer in an element over a barrier layer of the type described herein. Also typically present as dissolved solids in a photoconductor layer coating composition are a binder polymer and optional additives.

In general, such compositions may be prepared by blending the components together in a solvent liquid.

As the binder polymer, any hydrophobic organic polymer known to the photoconductive element art as a binder can be used These polymers are film forming and are preferably organic solvent soluble, and, in solid form, display dielectric strength and electrical insulating properties. Suitable polymers include, for example, styrene-butadiene copolymers; polyvinyl toluene-styrene copolymers; silicone resins; styrene alkyd resins; silicone-alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals), such as poly(vinyl butyryl); polyacrylic and methacrylic esters, such as poly(methyl methacrylate), poly(n-butyl methacrylate), poly(isobutyl methacrylate), etc.; polystyrene; nitrated polystyrene; polymethylstyrene; isobutylene polymers; polyesters, such as poly-[ethylene-co-alkylene-bis(alkylene-oxyaryl)-phenylenedicarboxylate]; phenolformaldehyde resins; ketone resins; polyamides; polycarbonates; polythiocarbonates; poly[ethylene-co-isopropylidene-2,2-bis(ethylene-oxyphenylene)terephthalate]; copolymers of vinyl haloarylates and vinyl acetate, such as poly(vinyl-m-bromobenzoate-co-vinyl acetate); chlorinated polyolefins such as chlorinated polyethylene; and the like. Preferred polymers are polyesters and polycarbonates.

One or more electron donor agents can also be added, such as 1,1-bis(4-di-p-tolylaminophenyl) cyclohexane, as taught in U.S. Pat. No. 4,127,412, tri-p-tolylamine, and the like. Coating aids, such as levelers, surfactants, cross linking agents, colorants, plasticizers, and the like, can also be added. The quantity of each of the respective additives present in a coating composition can vary, depending upon results desired and user preferences.

Presently preferred additives for a composition to be coated to form a charge generation layer are electron donor agents and surfactants.

Instead of a photoconductive agent being dispersed in a polymeric binder, a charge generation layer can, in some cases, depending upon the photoconductive agent involved, be comprised substantially entirely of only such an agent. For example, a perylene dicarboximide pigment of the Formula

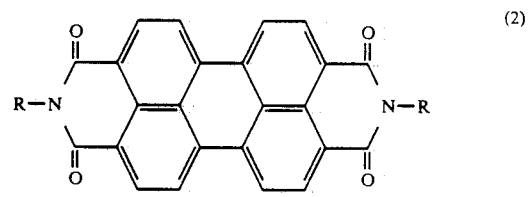

(2)

wherein R is an arylalkylene group, can be applied over an electrically conductive layer under vacuum by sublimination, such as under subatmospheric pressures of about $10^{-2}$ to about $10^{-5}$ mm Hg at temperatures in the range of about 200° to about 400° C.

A photoconductive charge generating layer composition coating is applied by coating the composition over the barrier layer using a technique such as above described for coating a barrier layer composition. After coating, the charge generating layer composition is conveniently air dried.

The charge transport layer is applied over the charge generation layer. When the charge transport layer contains at least one compound of Formula (1), a n-type charge transport layer is produced. An n-type charge transport layer accepts and transports negative charges (i.e., electrons).

A charge transport layer, if desired, can contain, in addition to at least one compound of Formula (1), at least one additional n-type charge transport agent of a type known to the art.

Representative of suitable known n-type charge transport agents are strong Lewis acids, such as organic, including metallo-organic, compounds containing one or more aromatic, including aromatically unsaturated heterocyclic, groups bearing an electron-withdrawing substituent. These are useful because of their electron-accepting capability. Typical electron withdrawing substituents include cyano; nitro; sulfonate; halogens, such as fluorine, chlorine, bromine and iodine; ketone groups; ester groups; acid anhydride groups; and other acid groups, such as carboxyl and quinone groups Representative n-type aromatic Lewis acids having electron-withdrawing substituents include phthalic anhydride, tetrachlorophthalic anhydride, benzil, mellitic anhydride, S-tricyanobenzene, picryl chloride, 2,4-dinitrochlorobenzene, 2,4-dinitrobromobenzene, 4-nitrobiphenyl, 4,4-dinitrobiphenyl, 2,4,6-trinitroanisole, trichlorotrinitrobenzene, trinitro-o-toluene, 4,6-dichloro-1,3-dinitrobenzene, 4,6-dibromo-1,3-dinitrobenzene, p-dinitrobenzene, chloranil, bromanil, 2,4,7-trinitro-9-fluorenone, 2,4,5,7-tetranitrofluorenone, trinitroanthracene, dinitroacridine, tetracyanopyrene, dinitroanthraquinone, and mixtures thereof.

Other useful n-type charge transports are conventional n-type organic photoconductors, for example, complexes of 2,4,6-trinitro-9-fluroeneone. Still others are the n-type photoconductors described in Research Disclosure, Vol. 109, May, 1973, pages 61-67, paragraph IV(a) (2) through (13).

In the charge transport layer, the charge transport agent(s) are dispersed, and preferably dissolved, in an electrically insulating organic polymeric film forming binder. In general, any of the polymeric binders heretofore described for use in the photoconductor art can be used, such as hereinabove described for use in a charge generation layer.

On a 100 weight percent total solids basis, a charge transport layer preferably is comprised of about 10 to about 60 weight percent of at least one Formula (1) compound and about 20 to about 80 weight percent of binder. Typically, a charge transport layer has a thickness in the range of about 3 to about 12 microns, although thicker and thinner such layers can be employed.

A charge transport layer of this invention can be produced in a bipolar form, if desired, by additionally incorporating thereinto at least one p-type transport agent. Such an agent preferentially accepts and transports positive charges (holes). A charge transport layer can contain more than one p-type charge transport or hole transport agent. If employed, the quantity of p-type transport agent(s) present in a charge transport layer on a total layer weight basis is preferably in the range of about 10 to about 50 weight percent, although larger and smaller quantities can be employed, if desired.

Examples of suitable p-type organic charge transport agents known to the prior art include:

1. Carbazoles including carbazole, N-ethyl carbazole, N-isopropyl carbazole, N-phenyl carbazole, halogenated carbazoles, various polymeric carbazole materials such as poly(vinyl carbazole), halogenated poly(vinyl carbazole), and the like.

2. Arylamines including monoarylamines, diarylamines, triarylamines and polymeric arylamines. Specific arylamine organic photoconductors include the nonpolymeric triphenylamines illustrated in U.S. Pat. No. 3,180,730; the polymeric triarylamines described in U.S. Pat. No. 3,240,597; the triarylamines having at least one of the aryl radicals substituted by either a vinyl radical or a vinylene radical having at least one active hydrogen-containing group, as described in U.S. Pat. No. 3,567,450; the triarylamines in which at least one of the aryl radicals is substituted by an active hydrogen-containing group, as described by U.S. Pat. No. 3,658,520; and tritolylamine.

3. Polyarylakanes of the type described in U.S. Pat. Nos. 3,274,000; 3,542,547; and 3,615,402. Preferred polyarylakane photoconductors are of the formula:

wherein:

D and G, which may be the same or different, each represent an aryl group, and J and E which may be the same or different, each represent hydrogen, an alkyl group, or an aryl group, and at least one of D, E and G contain an amino substituent.

An especially useful charge-transport material is a polyarylalkane wherein J and E are each hydrogen, aryl or alkyl, and D and G are each substituted aryl groups having as a substituent thereof a group of the formula:

wherein:

R is an unsubstituted aryl group, such as phenyl or alkyl-substituted aryl, such as a tolyl group. Examples of such polyarylalkanes may be found in U.S. Pat. No. 4,127,412.

4. Strong Lewis bases, such as aromatic compounds, including aromatically unsaturated heterocyclic compounds free from strong electron-withdrawing groups. Examples include tetraphenylpyrene, 1-methylpyrene, perylene, chrysene, anthracene, tetraphene, 2-phenyl naphthalene, azapyrene, fluorene, fluorenone, 1-ethylpyrene, acetyl pyrene, 2,3-benzochrysens, 3,4-benzopyrene, 1,4-bromopyrene, phenylindole, polyvinyl carbazole, polyvinyl pyrene, polyvinyltetracene, polyvinyl perylene and polyvinyl tetraphene.

5. Hydrazones, including the dialkyl-substituted aminobenzaldehyde-(diphenylhydrazones) of U.S. Pat. No. 4,150,987; alkylhydrazones and arylhydrazones as described in U.S. Pat. Nos. 4,554,231; 4,487,824; 4,481,271; 4,456,671; 4,446,217; and 4,423,129, which are illustrative of the p-type hydrazones.

Other useful p-type charge transports are the p-type photoconductors described in Research Disclosure, Vol. 109, May, 1973, pages 61-67 paragraph IV (A) (2) through (13).

Presently preferred p-type charge transport agents are carbazoles and arylamines.

In addition to an n-type or a p-type prior art charge transport agent and a binder polymer, a charge transport layer of this invention may contain various optional additives, such as surfactants, levelers, plasticizers, and the like.

On a 100 weight percent total solids basis, a charge transport layer can contain up to about 15 weight percent of such additives and preferably less than 1 weight percent of such additives.

The charge transport layer solid components are conveniently preliminarily dissolved in a solvent to produce a charge transport layer composition containing about 8 to about 15 weight percent solids with the balance up to 100 weight percent being the solvent. The solvents used can be those hereinabove described.

Coating of the charge transport layer composition over the charge generation layer can be accomplished using a coating technique such as hereinabove indicated. After coating, this charge transport layer composition is conveniently air dried.

If desired, a charge transport layer can be formed of two or more successive layers each of which has a different total solids composition. In such event at least one charge transport sublayer contains at least one compound of Formula (1).

Preferred photoconductor elements of this invention characteristically display dark decay values of not more than about 12 V/sec.

400 to about 600 volts. Thereafter, the rate of charge dissipation in volts per second is measured. The element is preliminarily dark adapted and maintained in the dark without activating radiation during the evaluation using ambient conditions of temperature and pressure.

Preferred photoconductor elements of this invention display reusability.

Those skilled in the art will appreciate that other variations in the structure of photoconductor elements incorporating a charge transport layer containing a compound of Formula (1) are possible and practical. For example, various different layer arrangements can be employed. Thus, a transport layer can be positioned, or "sandwiched", between two charge generation layers which can have the same or different respective compositions and layer thicknesses. Also, a charge generation layer can be positioned between two charge-transport layers only one of which may contain a compound of Formula (1).

Further, a charge transport layer of this invention can utilize, if desired, a polymeric binder which itself is a charge transport agent. Examples of such polymeric binders include poly(vinylcarbazole).

The invention is further illustrated by the following Examples:

EXAMPLE 1

Preparation of N,N'-Bis[p-(n-butyl)-phenyl]1,4,5,8-naphthalene bis(dicarboximide) (compound 3a)

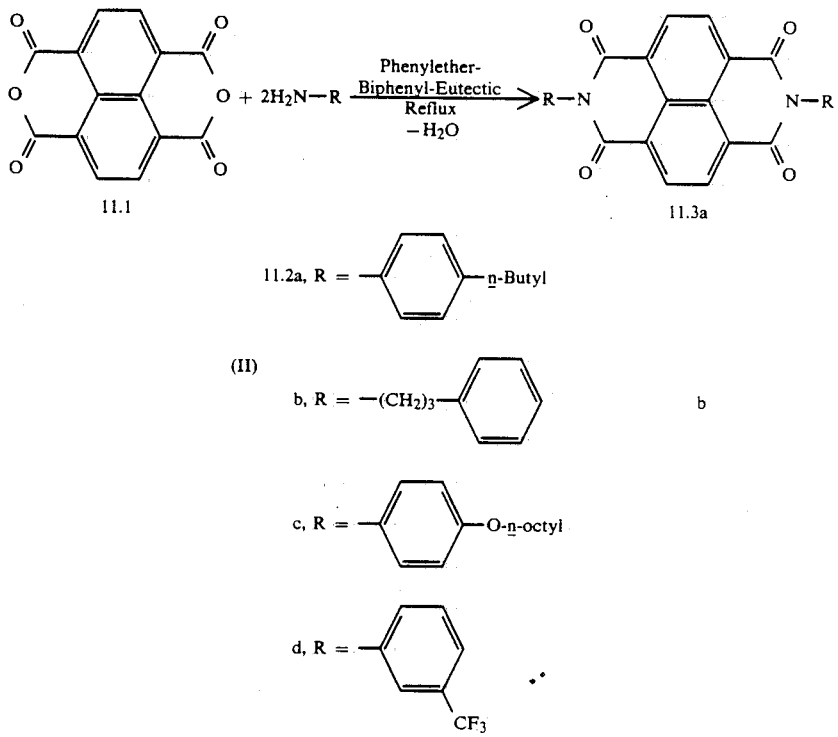

The term "dark decay" as used herein means the loss of electric charge from a charged photoconductor element under dark conditions and in the absence of activating radiation.

For present purposes of measuring dark decay, a multilayered photoconductor element of the type under consideration herein is charged upon its charge transport layer with a positive charge in the range of about A mixture of 30 g (0.11M) of 1,4,5,8-naphthalenetetracarboxylic dianhydride (compound 1) and 33.4 g (0.22M) of p-(n-butyl) aniline (compound 2a) in 500 mL of phenylether-biphenyl-eutectic (bp 258° C.) was azeotropically refluxed for 15 hours. After cooling to room temperature, the crystallized solid was filtered and washed with ether until the filtrate turned colorless, to give about 50 g of crude compound 3a. This was dissolved in 800 mL of hot chloroform; some activated charcoal was added, and the mixture cooled to room temperature. The mixture was filtered over Celite TM (a brand of diatomaceous earth available commercially from Johns Manville Corporation), and the clear, light brown filtrate was carefully concentrated on a steam bath to about 400 mL from which 40 g of compound 3a was obtained. Further purification was achieved by recrystallization from 2 L of p-dioxane to give 31 g (53%) of pure compound 3a as a slightly yellowish solid, melting point (mp) 358°-360° C.

EXAMPLE 2

Preparation of N,N'-Bis[3-phenylpropyl]1,4,5,8-naphthalene bis (dicarboximide) (compound 3b)

This compound was synthesized by the procedure of Example 1 except that 3-phenylpropylamine was used instead of p-(n-butyl)aniline, mp 217°-8° C.

EXAMPLE 3

Preparation of Photoconductor Element

A 0.15 micron thick charge-generation layer of ClIn (PcClx) chloroindium chlorophthalocyanine prepared pursuant to the procedure disclosed in U.S. Pat. No. 4,471,039 was prepared on a conductive nickel-coated poly(ethyleneterephthalate) film support which was prepared by vacuum deposition of nickel on 4 mil poly(ethyleneterephthalate) by vacuum sublimation from a resistance-heated tantalum boat at a rate of 20 Å/sec. Therefore, a 12 micron dry thickness charge-transport layer consisting on a total solids basis of 20 weight percent of compound 3a and 80 weight percent of a polyester binder (poly[4,4'-(2-norbornylidene) bis-phenylene terephthalate-co-azelate] 60/40), all dissolved in a 8 weight percent solution of chloroform, was produced by coating such solution over the charge generation layer.

The photoconductor element was corona charged to a positive surface potential in dark. The decrease of the surface potential in dark was termed as dark decay. After 1 or 2 seconds it was exposed to the monochromatic radiation of low intensity, 1-5 ergs/cm$^2$/sec. The photodischarge sensitivity, S, was determined by allowing the elements to discharge from 500 V a certain potential. The amount of radiation necessary to produce this discharge was calculated from the time required for the half-decay and the light intensity.

EXAMPLE 4

Preparation of Photoconductor Element

The charge-transport coating composition described in Example 3 was coated over approximately a 4 micron thick aggregate charge generation layer consisting of tri-p-tolylamine (40 weight percent), polycarbonate obtained from General Electric Co. as Lexan TM 145 (52 weight percent) and thiapyrylium sensitizing dye (4-(4'-dimethylaminophenyl)-2,6-diphenylthiapyrylium hexafluorophosphate) each (8.0%). The total film thickness was 10.5 microns and the aggregate material was confined to the charge generation layer. When the resulting photoconductor element was tested using the procedure described in Example 3, the following data were obtained:

TABLE I

| Charge Generation Layer | Charge Transport Layer | Sensitivity (S) 680 nm +500 V − 250 V |
|---|---|---|
| Aggregate | Binder (100%) Control | (did not discharge below 350 V) |
| Aggregate | Binder (80%) + 3a(20%) | 8.8 ergs/cm$^2$ |

This data indicates that compound 3a transports electrons and is very effective.

EXAMPLE 5

Preparation of Photoconductor Element

A 0.15 micron charge-generation layer was prepared in the manner described in Example 3 except that bromoindium phthalocyanine was used in place of the ClIn(PcClx). A charge transport layer (about 10 microns) containing compound 3b (20 weight percent) and poly[4,4'-(2-norbornylidene) bisphenylene terephthalateco-azelate]60/40 (80 weight percent) was coated over the charge-generation layer from an 8 weight percent chloroform solution. Dried samples of the resulting photoconductor element were tested as described above, and the sensitivity (S; at 800 nm) for discharge of from 500 V to 250 V was 45 ergs/cm$^2$.

EXAMPLE 6

Synthesis of Unsymmetrical
N-[p-(t-(Butyl)phenyl]-1,4,5,8-naphthalenecarboximide anhydride, Intermediate 30 g (0.11M) of 1,4,5,8-naphthalenetetracarboxylic dianhydride (compound 1) was added to 500 mL of phenyl ether-biphenyl eutectic (bp 258° C.) in a 1-L round-bottom flask. The mixture was heated to reflux with a heating mantle. The mantle was removed briefly, and 14.9 g (0.1M) p-(t-butyl)aniline added in one portion. The mixture was then refluxed for 18 hours with azeotropic removal of water via a Dean Stark trap. Approximately 250 mL of the solvent was then removed by distillation. The mixture was allowed to cool to room temperature and 500 mL diethyl ether added to the crystallized product. The product was filtered and washed with ether until the filtrate was colorless. The product was dissolved in 2L (liters) of hot chloroform with 8 g of decolorizing carbon. This mixture was filtered hot through a 1-in. pad of Celite in a steam-jacketed, coarse-sintered glass funnel. The yellow filtrate was concentrated on a rotary evaporator to yield 22 g of crude compound 4. This was used directly in the preparation of compound 5. An analytical sample was obtained by recrystallization from p-dioxane, which yielded a pale yellow solid: mp 345°-348° C., m/e 399M+, $^1$H NMR (CDCl$_3$) δ 1.3 (s,9H, t-Bu), 7.3 (ABq, 4H, ArH$_4$H$_S$ 8.8 (s, 4H, naphthyl).

EXAMPLE7

Synthesis of Unsymmetrical
N-[p-(t-Butyl)phenyl]-N'-[p-(N-butyl) phenyl]1,4,5,8-Naphthalenebix(dicarboximide) (Compound 5)

A mixture of 5.3 g (0.014M) compound 4 and 2.6 g (0.017M) p-(n-butyl)-aniline in 100 mL of phenyl ether-biphenyl eutectic was azeotropically refluxed over a Dean Stark trap for 18 hours. Approximately 50 mL of the solvent was removed by distillation, and after cooling to room temperature and diluting with 200 mL of diethyl ether, the crystallized product was filtered and washed with copious amount of ether. The solid was dissolved in 500 mL of hot chloroform containing 2 g of decolorizating charcoal. The mixture was filtered hot through a 1-in. pad of Celite in a steam-jacketed coarse sintered glass funnel. The yellow filtrate was concentrated on a rotary evaporator and recrystallized from p-dioxane to yield 5.0 g of a yellow solid: mp >380° C.; m/e 530 M+; $^1$H NMR (CDCl$_3$), 1.0 (t, 3H —CH$_2$C$\underline{H}$$_3$), 1.35 (s, 9H, t-Bu), 1.54 (m, 4H, —C$\underline{H}$$_2$—C$\underline{H}$$_2$—CH$_3$, 2.7 (t, 2H, Ar-C$\underline{H}$$_2$), 7.2, 7.35, 7.6, (m, 8H Ar$\underline{H}$$_A$$\underline{H}$$_B$), 8.8 (s, 4H, naphthyl).

EXAMPLE 8

Preparation of Photoconductor Element

Using the procedure of Example 4 but employing as the charge transport agent the compound 5 prepared in Example 7 (above), a photoconductor element is prepared. The change transport layer contains 40 weight % of compound 5 and 60 weight % of poly[4,4'-(2-norbornylidene) bisphenylene terephthalate-co-azelate] 60/40. The photoconductor element is characterized by sensitivity of I3.5 ergs/cm$^2$ discharging from 500 v to 100 v at 680 nm The foregoing specification is intended as illustrative and is not to be taken as limiting. Still other variations within the spirit and the scope of the invention are possible and will readily present themselves to those skilled in the art.

We claim:

1. A photoconductor element comprising in combination successive adhering layers of:

(a) a substrate;

(b) an electrically conductive layer;

(c) a charge generation layer and (d) a charge transport layer comprising a polymeric binder which is dissolved at least one cyclic bis-dicarboximide of the formula:

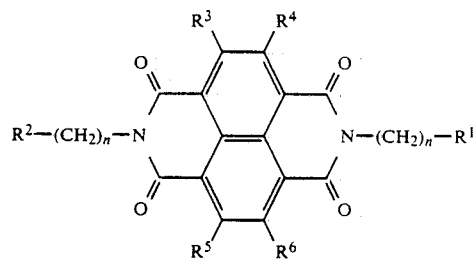

wherein:

R$^1$ and R$^2$, which may be the same or different, represent aryl, or aryl substituted with alkyl, alkoxy, perfluoroalkyl or perfluoroalkoxy groups having 2 to 20 carbon atoms; sulfonyl; sulfone; sulfonamide; nitrile; or nitro groups;

R$^3$, and R$^4$, R$^5$, and R$^6$, which may be the same or different, represent hydrogen, alkyl having 1 to 4 carbon atoms, alkoxy having 1 to 4 carbon atoms, or halogen; and n is 0 to 3.

2. The photoconductor element of claim 1 wherein said charge transport layer comprises about 20 to about 70 weight percent of said cyclic bis-dicarboximide and about 30 to about 80 weight percent of said binder on a 100 weight percent total charge transport layer basis.

3. The photoconductor element of claim 1 wherein said cyclic-bis-dicarboximide is N,N'-bis[p-(n-butyl)-phenyl]1,4,5,8-naphthalene bis(dicarboximide).

4. The photoconductor element of claim 1 wherein said cyclic bis-dicarboximide is N,N'-bis [3-phenylpropyl]1,4,5,8-naphthalene bis(dicarboximide).

5. The photoconductor element of claim 1 wherein said charge generation layer comprises a vapor deposited chloroindium chlorophthalocyanine bromindium phthalocyanine whose thickness is in the range of about 0.1 to about 0.5 microns.

6. The photoconductor element of claim 1 wherein the charge generation layer comprises a thiapyrylium aggregate having a thickness in the range of about 1 to about 6 microns.

7. The photoconductor element of claim 1 wherein said charge transport layer additionally contains incorporated thereinto a hole-transport agent.

8. The photoconductor element of claim 1 wherein a barrier layer is interposed between said charge generation layer and said electrically conductive layer.

9. The photoconductor element of claim 1 wherein a second charge generation layer is positioned over said charge transport layer.

10. A photoconductor element of claim 1 wherein the surface layer opposed to said substrate is overcoated with a polymeric protective overcoat.

* * * * *